United States Patent
Yokoyama et al.

(10) Patent No.: US 6,908,446 B2
(45) Date of Patent: Jun. 21, 2005

(54) BLOOD RESERVOIR

(75) Inventors: Kenji Yokoyama, Kanagawa (JP); Kazuhiko Takeuchi, Kanagawa (JP)

(73) Assignee: Termo Kabushiki Kaisha, Tokyo (JP)

( * ) Notice: Subject to any disclaimer, the term of this patent is extended or adjusted under 35 U.S.C. 154(b) by 413 days.

(21) Appl. No.: 09/997,171

(22) Filed: Nov. 30, 2001

(65) Prior Publication Data

US 2002/0094300 A1 Jul. 18, 2002

(30) Foreign Application Priority Data

Nov. 30, 2000 (JP) .................................. 2000-365086
May 7, 2001 (JP) .................................. 2001-136076

(51) Int. Cl.$^7$ .......................... A61M 37/00; A61M 1/36; B01D 69/08; C02F 9/00
(52) U.S. Cl. .................... 604/6.09; 422/44; 210/500.23; 210/259
(58) Field of Search .............................. 604/4.01, 5.01, 604/6.09, 6.15, 6.11; 210/503, 323.1, 188, 416.1, 433.1, 434, 436, 500.21, 500.23, 506, 252, 259; 422/44, 48

(56) References Cited

U.S. PATENT DOCUMENTS

| | | |
|---|---|---|
| 4,054,523 A | 10/1977 | Ingenito et al. |
| 4,642,089 A | 2/1987 | Zupkas et al. |
| 5,039,430 A | 8/1991 | Corey, Jr. |
| 5,039,482 A | 8/1991 | Panzani et al. |
| 5,049,146 A | 9/1991 | Bringham et al. |
| 5,800,721 A | 9/1998 | McBride |
| 5,823,986 A | 10/1998 | Peterson |
| 5,849,186 A | 12/1998 | Raneri et al. |
| 5,919,153 A * | 7/1999 | Van Driel .................. 604/6.15 |
| 6,475,176 B2 * | 11/2002 | Fini .......................... 604/6.15 |

FOREIGN PATENT DOCUMENTS

JP   5-317420 A   12/1993

* cited by examiner

Primary Examiner—Angela D. Sykes
Assistant Examiner—Leslie R. Deak
(74) Attorney, Agent, or Firm—Burns, Doane, Swecker & Mathis, L.L.P.

(57) ABSTRACT

A blood reservoir being capable of reducing damage to blood stored therein. The blood reservoir has a housing in the form of a box, and filtering and defoaming devices provided in the housing, i.e., a device for filtering and defoaming on blood suctioned from a surgical field (outside a heart), a device for filtering and defoaming on blood vented from the interior of the heart, and a device for filtering and defoaming on blood drawn off from a large vein. The vented blood flowing into the blood reservoir passes through a vented blood filtering member to be introduced into a blood storage space without contacting an antifoaming agent and foreign substances filtered off from the suctioned blood.

26 Claims, 9 Drawing Sheets

BLOOD RESERVOIR

BACKGROUND OF THE INVENTION

1. Field of the Invention

The present invention relates to a blood reservoir.

2. Description of the Related Art

For example, in open heat surgery, an extracorporeal blood circulation is performed in such a manner that blood is drawn off from veins (large veins) of a patient, gas change is performed on the blood by an oxygenator, and the blood is returned to the arterial system of the patient by driving a blood pump.

An extracorporeal blood circulation system includes a main circuit having a blood return line from large veins and a blood return line to the arterial system, a suction circuit for suctioning blood accumulated in a surgical field, and a vent circuit for suctioning blood accumulated in a heart.

In these suction and vent circuits, blood suctioned from the surgical field (outside the heart) and vented blood suctioned from the interior of the heart are introduced into a blood reservoir (cardiotomy reservoir) for temporarily storing the blood suctioned from these regions. A filtering member provided in the blood reservoir filters off foreign substances from the blood and removes bubbles from the blood. The blood which has undergone filtering and bubble removal in the blood reservoir is returned to the body of the patient. The blood reservoir also has a buffering function for constantly maintaining the blood return rate by regulating the blood volume in the circuits.

In blood caused to flow into the above-described blood reservoir, blood suctioned from the outside of the heart contains comparatively large amounts of foreign substances such as fat droplets, tissue fragments, denatured proteins and aggregates other than the ordinary blood contents. On the other hand, blood vented from the interior of the heart ordinarily has smaller contents of such foreign substances and is less damaged and generally the same as blood drawn off from large veins.

The conventional blood reservoir is constructed such that blood suctioned from the outside of the heart and blood vented from the interior of the heart are filtered by a common filtering member after their confluence in the blood reservoir. Before and during the passage of the vented blood through the filtering member in the blood reservoir, therefore, the least damaged vented blood contacts foreign substances filtered off from the suctioned blood and becomes activated by reaction with the foreign substances.

SUMMARY OF THE INVENTION

An object of the present invention is to provide a blood reservoir capable of reducing damage to blood stored therein.

The above-mentioned object can be achieved by the following items (1) to (21) of the present invention.

(1) A blood reservoir characterized in that:

which comprises:

a housing having a vented blood inlet through which blood vented from the interior of a heart flows in, a suctioned blood inlet through which blood suctioned from the outside of the heart flows in, and a blood outlet; and a filtering unit provided in the housing, the filtering unit having a filtering member for filtering the blood flowing in; and that the vented blood flowing into the housing can pass through the filtering member without contacting foreign substances filtered off from the suctioned blood.

(2) A blood reservoir as described in the item (1), further comprising a vented blood filtering chamber communicating with the vented blood inlet and formed at least partially by the filtering member forming a vented blood filtering member, and a suctioned blood filtering chamber communicating with the suctioned blood inlet and formed at least partially by the filtering member forming a suctioned blood filtering member.

(3) A blood reservoir as described in the item (2), in which the vented blood filtering chamber and the suctioned blood filtering chamber are formed by using a partition to separate a space encircled by the same filtering member into two.

(4) A blood reservoir as described in the item (2), in which the vented blood filtering chamber and the suctioned blood filtering chamber are formed by separate filtering members.

(5) A blood reservoir characterized in that:

which comprises:

a housing having a vented blood inlet through which blood vented from the interior of a heart flows in, a suctioned blood inlet through which blood suctioned from the outside of the heart flows in, and a blood outlet;

a vented blood filtering unit provided in the housing, the vented blood filtering unit having a vented blood filtering member for filtering the vented blood flowing in through the vented blood inlet;

a suctioned blood filtering unit provided in the housing, the vented blood filtering unit having a suctioned blood filtering member for filtering the suctioned blood flowing in through the suctioned blood inlet; and an antifoaming agent placed in the suctioned blood filtering unit, the antifoaming agent placed at a position which is capable of contacting the suctioned blood flowing in through the suctioned blood inlet; and that the vented blood flowing in through the vented blood inlet can pass through the vented blood filtering member without contacting the antifoaming agent and foreign substances filtered off from the suctioned blood.

(6) A blood reservoir as described in the item (4) or (5), in which at least one condition set in the vented blood filtering member and at least one condition set in the suctioned blood filtering member are different from each other.

(7) A blood reservoir as described in the item (5) or (6), in which the vented blood filtering member comprises a screen filter.

(8) A blood reservoir as described in any one of the items (5) to (7), in which the suctioned blood filtering member comprises a depth filter.

(9) A blood reservoir as described in any one of the items (4) to (8), in which the suctioned blood filtering member comprises nonwoven fabric.

(10) A blood reservoir as described in any one of the items (2) to (9), in which the effective area of the vented blood filtering member and the effective area of the suctioned blood filtering member are different from each other.

(11) A blood reservoir as described in any one of the items (1) to (10), further comprising defoaming means retained on the filtering member and/or a retaining member.

(12) A blood reservoir as described in any one of the items (1) to (10), in which the antifoaming agent is retained on a retaining member provided in the suctioned blood filtering unit and/or on the suctioned blood filtering member.

(13) A blood reservoir as described in any one of the items (5), (6), (7), (8), (9), (10) and (12), in which the antifoaming agent is also provided below a maximum blood level.

(14) A blood reservoir as described in any one of the items (1) to (13), in which the vented blood filtering unit has an antifoaming agent placed at a position above the maximum blood level such that the vented blood flowing in through the vented blood inlet does not contact the antifoaming agent in an ordinary situation.

(15) A blood reservoir as described in the item (11), further comprising:

antifoaming agent retained on the filtering member forming the vented blood filtering chamber and/or on a retaining member placed on the vented blood filtering chamber; and antifoaming agent retained on the filtering member forming the suctioned blood filtering chamber and/or on a retaining member placed on the suctioned blood filtering chamber, in which the total amounts of the retained antifoaming agents are different from each other.

(16) A blood reservoir as described in any one of the items (2) to (15), further comprising a vented blood lead-in tube for leading blood from the vented blood inlet into the vented blood filtering chamber, and a suctioned blood lead-in tube for leading blood from the suctioned blood inlet into the suctioned blood filtering chamber.

(17) A blood reservoir as described in the item (16), in which the vented blood lead-in tube is arranged so as to extend downward relative to the suctioned blood lead-in tube.

(18) A blood reservoir as described in any one of the item (2) to (17), in which the housing further has a venous blood inlet through which blood from a large vein flows in, and a venous blood filtering unit having a venous blood filtering member for filtering blood flowing through the venous blood inlet is provided in the housing.

(19) A blood reservoir as described in any one of the items (6), (10) and (11), in which the venous blood filtering member has a venous blood filtering chamber formed at least partially by the filtering member.

(20) A blood reservoir as described in the item (18), in which the same kind of filtering member as the venous blood filtering member is used as the vented blood filtering member.

(21) A blood reservoir as described in the item (1), in which the housing has a venous blood inlet through which blood from a large vein flows in, and a venous blood filtering chamber communicating with the venous blood inlet and formed at least partially by the filtering member.

DESCRIPTION OF THE PREFERRED EMBODIMENTS

Blood reservoirs in preferred embodiments of the present invention will be described below in detail with reference to the accompanying drawings.

<First Embodiment>

Figure 1:
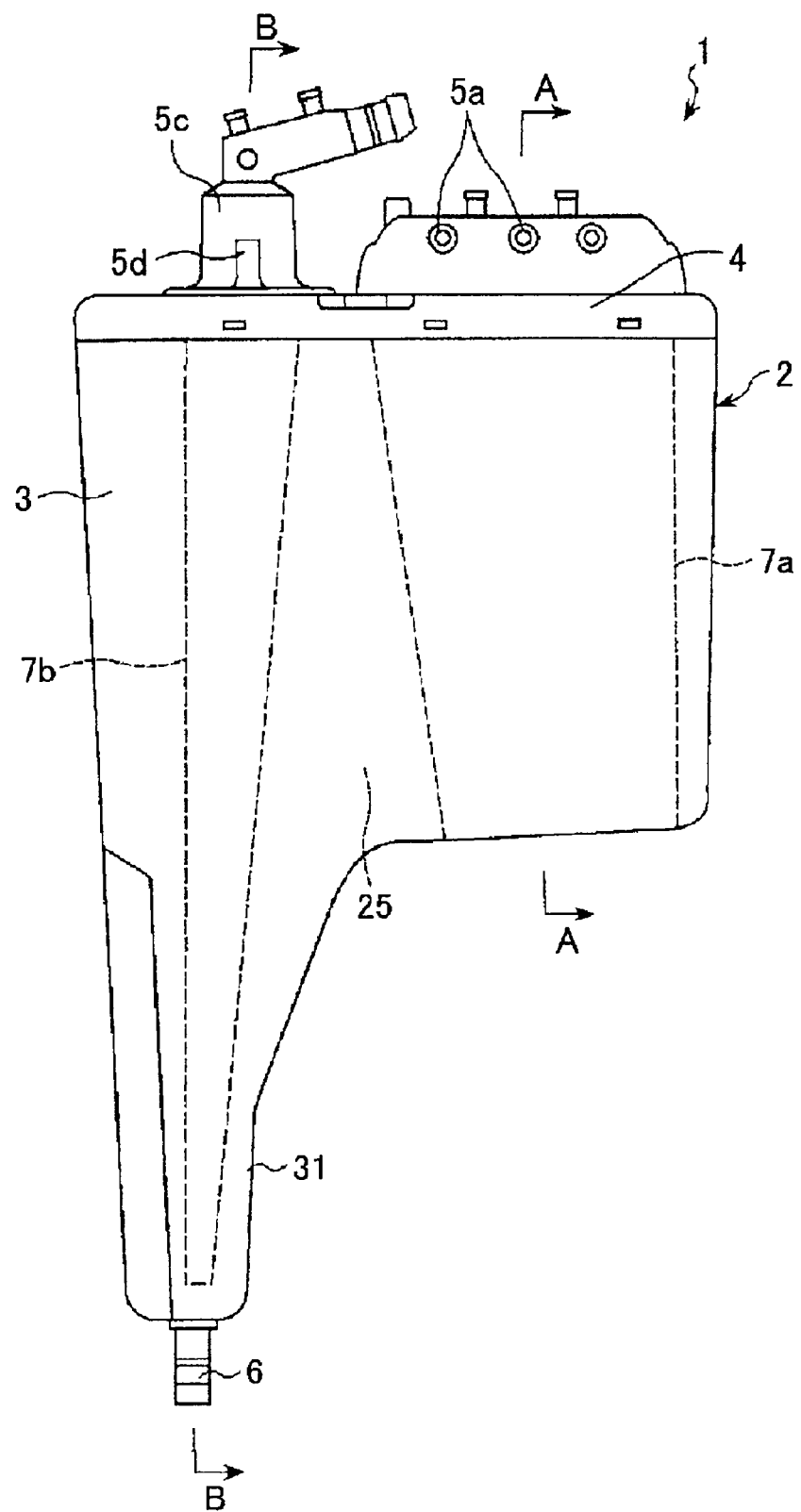
FIG. 1 is a side view of a blood reservoir which represents a first embodiment of the present invention.
Figure 2:
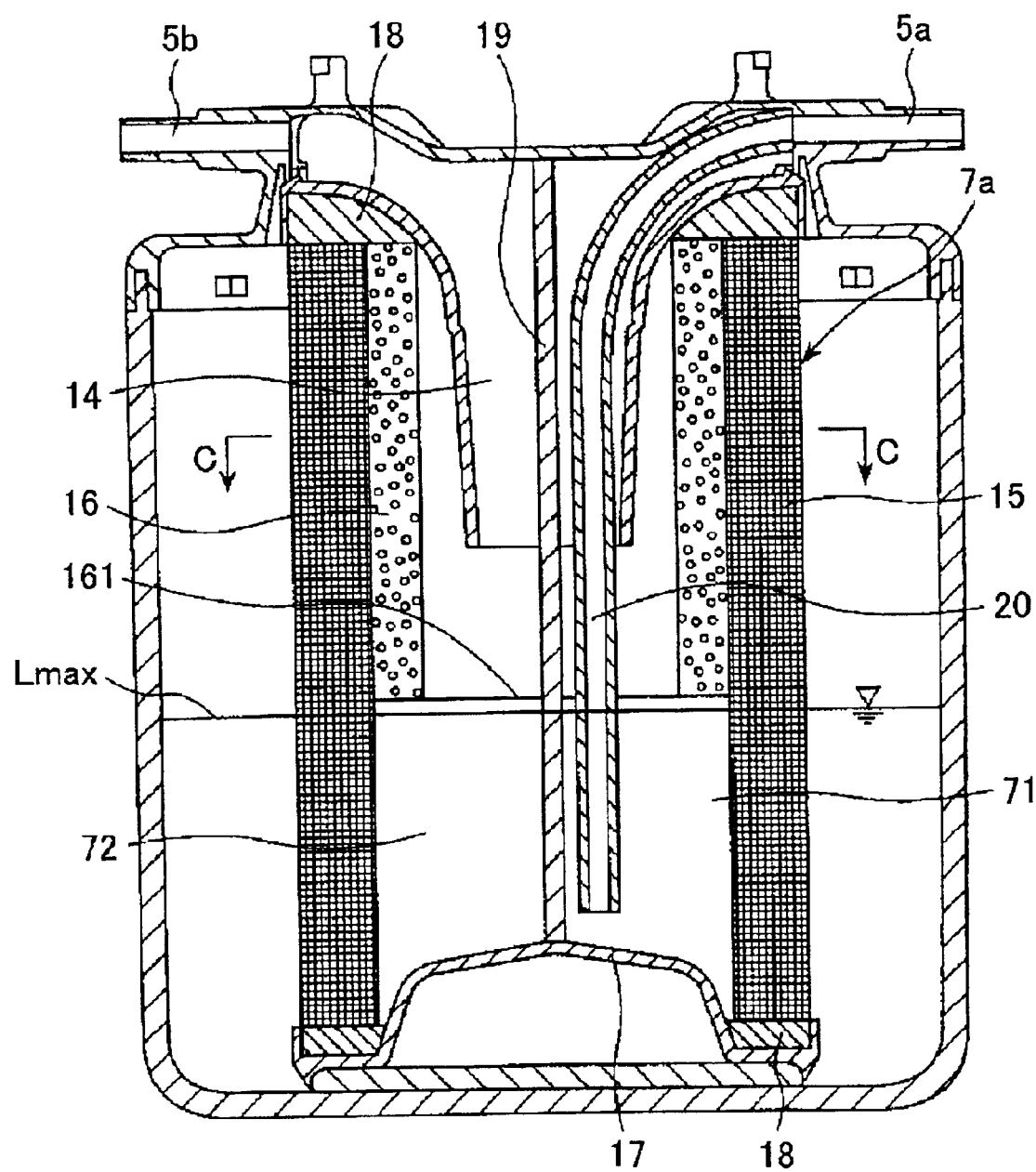
FIG. 2 is a cross-sectional view taken along the line A—A of FIG. 1.
Figure 3:
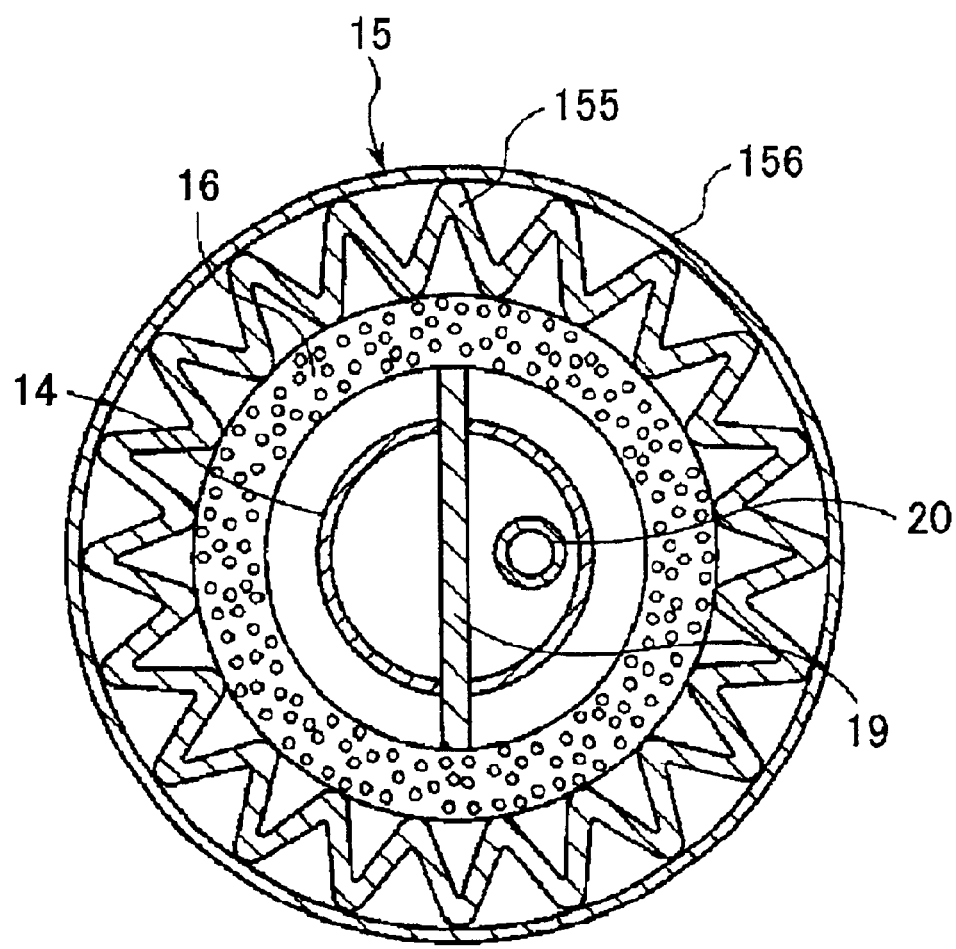
FIG. 3 is a cross-sectional view taken along the line C—C of FIG. 2.
Figure 4:
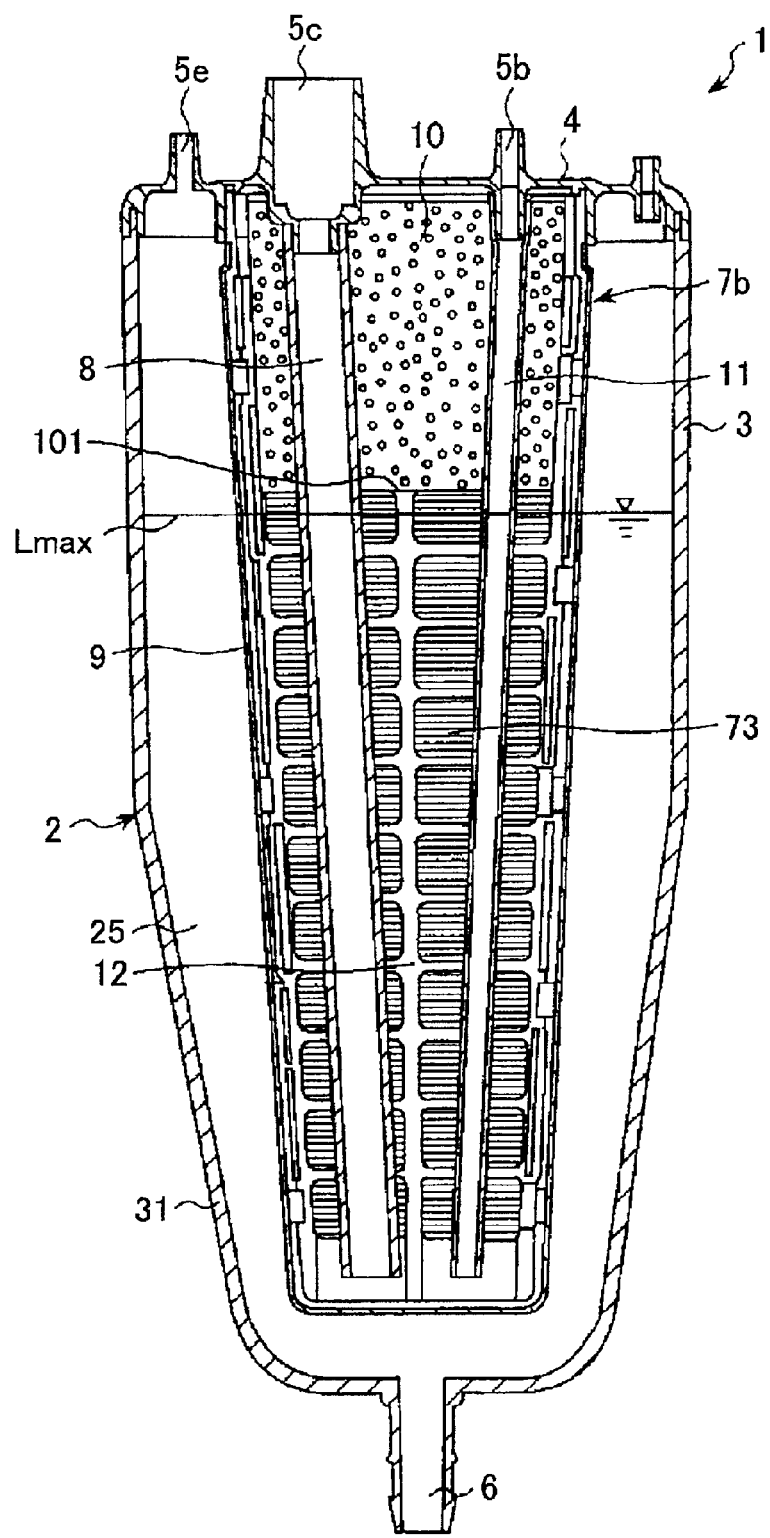
FIG. 4 is a cross-sectional view taken along the line B—B of FIG. 1.
Figure 5:
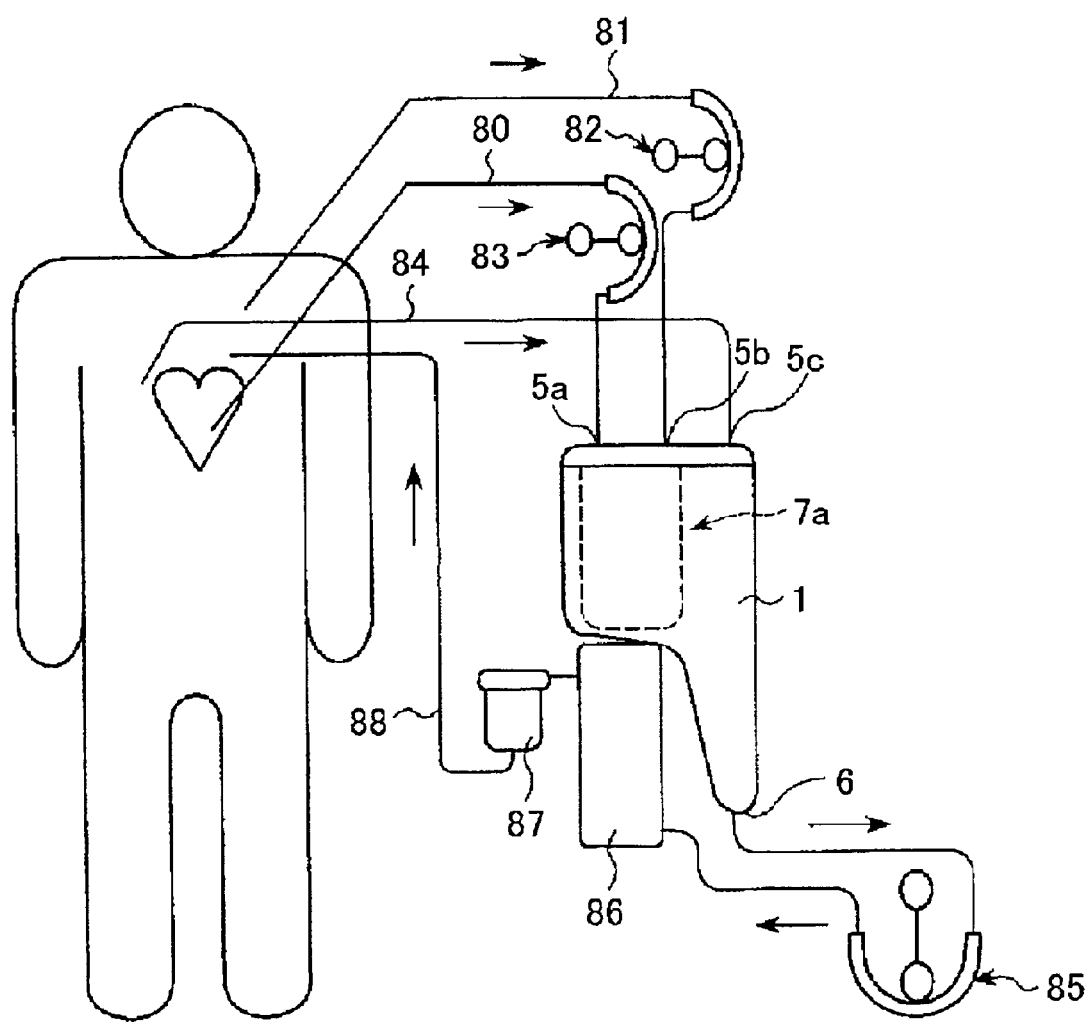
FIG. 5 is a circuit diagram showing an extracorporeal blood circulation.

A blood reservoir which represents a first embodiment of the present invention will be described with reference to FIGS. 1 through 5. FIG. 1 is a side view of a blood reservoir which represents the first embodiment of the present invention, FIG. 2 is a cross-sectional view taken along the line A—A of FIG. 1, FIG. 3 is a cross-sectional view taken along the line C—C of FIG. 2, FIG. 4 is a cross-sectional view taken along the line B—B of FIG. 1, and FIG. 5 is a circuit diagram showing an extracorporeal blood circulation.

In FIG. 1, reference numeral 1 indicates a blood reservoir; 2, a housing; 3, a housing body; 4, a lid; 5a, a vented inlet; 5c, a venous blood inlet; 5d, a priming solution inlet; 6, a blood outlet; 7a and 7b, filtering and defoaming devices; 25, a blood reservoir space; and 31, a projecting portion.

In FIG. 1, the blood reservoir 1 is constructed by integrally combining a reservoir for temporarily storing blood drawn off from large veins and a reservoir (cardiotomy reservoir) for temporarily storing blood suctioned from the outside of a heart and blood vented from the interior of the heart. The blood reservoir 1 has a housing 2 formed by a housing body 3 and a lid 4. A blood reservoir space 25 for storing blood is formed in the housing 2.

The housing body 3 is formed into the shape of a box and has a projecting portion 31 which projects downward. A cylindrical blood outlet 6 communicating with the blood reservoir space 25 is formed below the projecting portion 31.

The lid 4 is fitted to an upper end portion of the housing body 3 so as to cover a top opening of the housing body 3. Cylindrical blood inlets 5a (vented blood inlet), 5b (suctioned blood inlet), and 5c (venous blood inlet) are formed at predetermined positions in the lid 4.

The blood inlets 5a to 5c and the blood outlet 6 are connected in an extracorporeal blood circulation circuit, as described below.

In FIG. 5, reference numeral 1 indicates a blood reservoir; 5a, a vented blood inlet; 5b, a suctioned blood inlet; 5c, a venous blood inlet; 6, a blood outlet; 7a, a filtering and defoaming device; 80, a vent suction line; 81, an intracardiac (intrathoracic) suction line; 82 and 83, pumps; 84, a blood drawing line; 85, a blood pump; 86, an oxygenator; 87, an arterial filter; and 88, a blood return line.

Referring to FIG. 5, a tube in a vent suction line 80 is connected to the vented blood inlet 5a. That is, blood suctioned from the interior of the heart (from the left atrium and the left ventricle of the heart in particular) by a pump 83 (hereinafter referred to as "vented blood") flows into the blood reservoir 1 through the vented blood inlet 5a. This vented blood is less damaged blood in which the contents of foreign substances such as fat droplets, tissue fragments, denatured proteins and aggregates other than the ordinary blood contents are comparatively small. Also, the amount of bubbles contained in the vented blood is comparatively small.

A tube in an intracardiac (intrathoracic) suction line 81 is connected to the suctioned blood inlet 5b. That is, blood suctioned from a surgical field such as an intracardiac (intrathoracic) region (the outside of the heart) by a pump 82 (hereinafter referred to as "suctioned blood") flows into the blood reservoir 1 through the suctioned blood inlet 5b. This suctioned blood has comparatively large contents of foreign substances such as those mentioned above, and also contains a comparatively large amount of bubbles.

A tube in a blood drawing line 84 is connected to the venous blood inlet 5c. That is, blood drawn off from the large veins flows into the blood reservoir 1 through the venous blood inlet 5c.

Filtering and defoaming devices 7a and 7b described below remove foreign substances and bubbles from the blood flowing into the blood reservoir 1 through the inlets 5a to 5c. Thereafter the blood flows out through the blood outlet 6.

A tube in a line connected to an oxygenator 86 is connected to the blood outlet 6. A blood pump 85 is provided in an intermediate portion of this line.

Blood oxygenated by the oxygenator 86 flows through a tube forming a blood return line 88 to be fed into the arterial system. An arterial filter 87 is provided in an intermediate portion of the blood return line.

Referring to FIG. 4, a priming solution inlet 5d used to inject a priming solution into the filtering and defoaming device 7b described below is formed in the lid 4 by the side of the venous blood inlet 5c.

An air release port 5e is formed in the lid 4 by the side of the venous blood inlet 5c opposite from the priming solution inlet 5d. Part of air generated from bubbles broken by the filtering and defoaming devices 7a and 7b described below is released to the outside through the air release port 5e. Air is enabled to enter or exit through the air release port 5e in accordance with the increase and decrease in the amount of blood in the blood reservoir 1.

No particular limitation is imposed on the selection of the capacity of the reservoir space 25 in the above-described housing 2. However, it is preferred that the capacity be set to about 3000 to 5000 ml for adults and to about 1000 to 2500 ml for young children.

The material of each of the housing body 3 and the lid 4 may be selected from polycarbonate, an acrylic resin, polyethylene terephthalate, polyethylene, polypropylene, polystyrene, polyvinyl chloride, acrylic-styrene copolymer, acrylic-butadiene-styrene copolymer, and the like. Among these materials, polycarbonate, an acrylic resin, polystyrene and polyvinyl chloride are particularly preferable.

Preferably, the housing body 3 and the lid 4 are made substantially transparent to be enable the amount of stored blood, the state of blood, etc., in the housing to be visually checked.

Preferably, a scale (not shown) for indicating the amount of stored blood is provided on a front surface (an end surface on the left-hand side as viewed in FIG. 1) or a side surface of the housing body 3.

In the thus-constructed blood reservoir 1 are provided two filtering and defoaming devices 7a and 7b for removing foreign substances and bubbles contained in blood flowing into the reservoir space 25. The construction of each of the filtering and defoaming devices 7a and 7b will be described.

The filtering and defoaming device 7a constitutes a cardiotomy filter. Blood vented from the vented blood inlet 5a and blood suctioned from the suctioned blood inlet 5b flow into this filter.

In FIG. 2, reference numeral 5a indicates a vented blood inlet; 5b, a suctioned blood inlet; 7a, a filtering and defoaming device; 14, a suctioned blood lead-in tube; 15, a filtering member; 16, a defoaming member; 17, a blood distributing member; 18, a potting material; 19, a partition; 20, a vented blood lead-in tube; 71, a vented blood filtering chamber; 72, a suctioned blood filtering chamber; and 161, a lower end surface of the defoaming member.

Referring to FIG. 2, the filtering and defoaming device 7a has a vented blood lead-in tube 20 connected to the vented blood inlet 5a, a suctioned blood lead-in tube 14 connected to the suctioned blood inlet 5b, a filtering member 15, a defoaming member 16 placed along the inner surface of an upper portion of the filtering member 15, a blood distributing member 17, and a partition 19.

The term "a filtering and defoaming device" in the description of the present invention refers to a filtering unit having a defoaming member (also having a filtering member, a lead-in tube, and, if necessary, a blood distributing member and a partition) or refers only to a filtering unit.

The suctioned blood lead-in tube 14 is a tubular member extending downward and generally vertically while being gradually reduced in inside diameter. An upper end portion of the suctioned blood lead-in tube 14 communicates with the suctioned blood inlet 5b. The lower end of the suctioned blood lead-in tube 14 is positioned slightly higher than a lower end surface 161 of the defoaming member 16. Blood (suctioned blood) caused to flow into the suctioned blood lead-in tube 14 from the suctioned blood inlet 5b falls from the lower end of the suctioned blood lead-in tube 14, thus being supplied to the interior of the filtering and defoaming device 7a without being brought into contact with the defoaming member 16. Since the lower end of the suctioned blood lead-in tube 14 is at a comparatively higher position (higher than the lower end of the vented blood lead-in tube 20), it is not submerged in the blood in the filtering and defoaming device 7a even when the liquid surface of blood is heightened to a certain level by foreign substances filtered off by the filtering member 15, thereby suppressing foaming.

The upper end of the vented blood lead-in tube 20 communicates with the vented blood inlet 5a. Preferably, the lower end of the vented blood lead-in tube 20 is extended downward relative to the lower end of the suctioned blood lead-in tube 14. If the vented blood lead-in tube 20 is formed in this manner, blood falling from the lower end of the vented blood lead-in tube 20 impinges softly on the blood distributing member 17, thus reducing the amount of foaming.

The material of each of the suctioned blood lead-in tube 14 and the vented blood lead-in tube 20 may be selected from polymeric materials, e.g., polycarbonate, an acrylic resin, polyethylene terephthalate (PET), polybutylene terephthalate (PBT), polyethylene, polypropylene, polystyrene, polyvinyl chloride, acrylic-styrene copolymer, and acrylic-butadiene-styrene copolymer, various glasses, various ceramics, e.g., alumina and silica, metals, e.g., stainless steel, aluminium, copper, and titanium, various carbon materials, or may be selected as a combination of two or more of these materials. Among these materials, polyvinyl chloride, polycarbonate, polystyrene, PET and stainless steel are particularly preferable.

The filtering member 15, which preferably has a cylindrical shape, is placed around the suctioned blood lead-in tube 14 and the vented blood lead-in tube 20 formed as described above. The filtering member 15 has the function of removing foreign substances and bubbles from blood.

The filtering member 15 is formed of a porous material having sufficiently high blood permeability. Examples of such a porous material are a mesh (net), woven fabric, and nonwoven fabric. One of these members or a combination of any of these members (in stacked form in particular) may be used. According to the present invention, it is preferable to include nonwoven fabric in the filtering member 15, because nonwoven fabric has high blood permeability and capable of effectively removing foreign substances from blood.

The material of the filtering member 15, particularly the material of nonwoven fabric may be selected from polymeric materials, e.g., polyesters, such as PET and PBT, nylon (polyamide), Tetron, Rayon, polyolefins, such as polypropylene and polyethylene, and polyvinyl chloride, or may be selected as a combination of two or more of these materials. Among these materials, polyester, polypropylene and polyethylene are particularly preferable.

The filtering member 15 may be processed by a hydrophilization treatment such as a plasma treatment or coating with a hydrophilic polymeric material to further improve its blood permeability. In such a case, a hydrophilization treatment such as a plasma treatment may be performed on the basis of an ordinary method.

In FIG. 3, reference numeral 14 indicates a suctioned blood lead-in tube; 15, a filtering member; 16, a defoaming member; 19, a partition; 20, a vented blood lead-in tube; 155, an inner layer; and 156, an outer layer.

The filtering member 15 has an inner layer 155 formed by folding (pleating) the above-mentioned constituent member, and an outer layer 156 bonded to the peripheral surface of the inner layer 155.

Since the inner layer 155 is formed so as to have folds, the filtering member 15 can have a sufficiently large effective area. The outer layer 156 has the function of maintaining the filter member 15 in a predetermined shape by limiting deformation of the inner layer 155 between the outer layer 156 and the defoaming member 16. A mesh, a net or a frame member having a comparatively high hardness is preferably used as the outer layer 156.

The blood distributing member 17 is mounted at the lower end opening of the filtering member 15 so as to project toward the inside of the filtering and defoaming device 7a. The blood distributing member 17 has the function of distributing blood falling from the lower end of the suctioned blood lead-in tube 14 to the inner surface of the filtering member 15.

The lower end of the filtering member 15 is fixed to a peripheral portion of the blood distributing member 17 by a potting material 18. The upper ends of the filtering member 15 and the defoaming member 16 are fixed to a base portion of the suctioned blood lead-in tube 14 by a potting material 18.

Preferably, the defoaming member 16 on which an antifoaming agent is retained is placed along the inner surface of an upper portion of the filtering member 15. It is possible to remove bubbles more reliably by the defoaming member 16 retaining an antifoaming agent. The antifoaming agent retained on the defoaming member 16 has the function of breaking bubbles when the bubbles are brought into contact with it. A typical example of the antifoaming agent is silicone (a compound type of silicone with which silica is blended, an oil type of silicone, or the like).

Such an antifoaming agent is retained on the defoaming member 16 by, for example, a method of impregnating the constituent member with a solution containing antifoaming agent or applying or spraying the solution to the member, and drying the member (at 30° C. for 180 minutes, for example).

The material of the defoaming member 16 may be selected from various porous materials, e.g., foamed materials, such as polyurethane foam, polyethylene foam, polypropylene foam and polystyrene foam, mesh, woven fabric, nonwoven fabric, and sintered materials, such as porous ceramics and resins. Among these materials, one having comparatively low resistance to passage of blood (or a low pressure loss) is preferred.

If a foamed material, such as polyurethane foam or some other porous material is used as a material of low blood passage resistance, the pore size is preferably about 20 $\mu$m to 5 mm and, more preferably, about 30 $\mu$m to 2 mm.

Preferably, the position of the lower end surface 161 of the defoaming member 16 is set close to or higher than the blood level (maximum blood level Lmax) reached by the maximum storable blood amount, i.e., the maximum amount of blood storable in the blood reservoir 1.

The maximum storable blood amount is a blood amount limit beyond which the amount of blood is so large that a risk of an overflow of blood from the blood reservoir 1 arises. Ordinarily, the maximum storable blood amount is about 70 to 100% of the effective capacity of the reservoir space 25, depending on the functions and structure of the blood reservoir 1.

The same antifoaming agent as that described above may be retained on the filtering member 15 (on an upper portion thereof in particular) by the same retention method.

The partition 19 is provided inside the filtering member 15 so as to extend in the axial direction (top-bottom direction). The space inside the filtering member 15 is thereby sectioned into a vented blood filtering chamber 71 on the right-hand side as viewed in FIG. 2 and a suctioned blood filtering chamber 72 on the left-hand side as viewed in FIG. 2. That is, the vented blood filtering chamber 71 is defined between (surrounded by) the partition 19 and the portion of the filtering member 15 on the right-hand side as viewed in FIG. 2. The suctioned blood filtering chamber 72 is defined between (surrounded by) the partition 19 and the portion of the filtering member 15 on the left-hand side as viewed in FIG. 2.

The vented blood lead-in tube 20 is positioned in the vented blood filtering chamber 71 to enable inflow of blood vented from the vented blood inlet 5a. The suctioned blood lead-in tube 14 is positioned in the suctioned blood filtering chamber 72 to enable inflow of blood suctioned from the suctioned blood inlet 14. That is, vented blood and suctioned blood flowing into the filtering and defoaming device 7a do not contact each other before the passage of blood through the filtering member 15.

The above-described arrangement ensures that vented blood flowing into the filtering and foaming device 7a passes through the filtering member 15 without contacting foreign substances such as fat droplets, tissue fragments, denatured proteins and aggregates other than the ordinary blood contents, filtered off from suctioned blood by the filtering member 15. Therefore the vented blood is not activated by interaction with above-mentioned foreign substances and is maintained in a less damaged state. Consequently, total damage to blood to be fed (returned) after temporary storage in the blood reservoir 1 is reduced, thereby reducing harmful effects on the living body.

The filtering and defoaming device 7b will next be described. The same details as those of the filtering and defoaming device 7a will not be repeated.

In FIG. 4, reference numeral 1 indicates a blood reservoir; 2, a housing; 3, a housing body; 4, a lid; 5c, a venous blood inlet; 5d, a priming solution inlet; 5e, an air release port; 6, a blood outlet; 7b, a filtering and defoaming device; 8, a venous blood lead-in tube; 9, a venous blood filtering member; 10, a defoaming member; 11, a priming solution lead-in tube; 12, a frame member; 25, a blood reservoir space,; 31, a projecting portion; 73, a venous blood filtering chamber; and 101, a position.

Referring to FIG. 4, the filtering and defoaming device 7b has a venous blood lead-in tube 8 connected to the venous blood inlet 5c, a venous blood filtering member 9, and a defoaming member 10 placed above the venous blood filtering member 9. In the filtering and defoaming device 7b, a venous blood filtering chamber 73 is formed by the venous blood filtering member 9. The venous blood filtering chamber 73 communicates with the venous blood inlet 5c through the venous blood lead-in tube 8. The thus-constructed filtering and defoaming device 7b removes bubbles and foreign substances contained in blood drawn off from large veins.

The venous blood lead-in tube 8 is a straight tube extending generally vertically and having its upper end connected to the venous blood inlet 5c. The lower end of the venous blood lead-in tube 8 is extended to the vicinity of an inner bottom portion of the filtering and defoaming device 7b to ensure that blood caused to flow into the venous blood lead-in tube 8 from the venous blood inlet 5c is supplied to the interior of the filtering and defoaming device 7b without being brought into contact with the defoaming member 10 described below, thereby preventing mixing of an antifoaming agent into the blood when the blood flows into the filtering and defoaming device 7b.

A priming solution lead-in tube 11 having a diameter smaller than that of the venous blood lead-in tube 8 is provided in the filtering and defoaming device 7b. The upper end of the priming solution lead-in tube 11 is connected to the priming solution inlet 5d. The lower end of the priming solution lead-in tube 11 is extended to the vicinity of an inner bottom portion of the filtering and defoaming device 7b, as is the venous blood lead-in tube 8.

The venous blood filtering member 9 and the defoaming member 10 are placed around the venous blood lead-in tube 8 and the priming solution lead-in tube 11 formed as described above.

Preferably, the venous blood filtering member 9 is formed of the same material as that described above. A filtering member including a mesh is particularly preferred, because a mesh has high blood permeability and high opening accuracy and is capable of effectively removing bubbles, etc.

The mesh may be a sheet of mesh in which meshes are regularly arrayed, and which is provided in the form of woven fiber cloth or knitting, an integrally formed member, a worked member, or the like.

The material of the venous blood filtering member 9, particularly the material of the mesh may be selected from polymeric materials, e.g., polyesters, such as PET and PBT, nylon (polyamide), Tetron, Rayon, polyolefins, such as polypropylene and polyethylene, and polyvinyl chloride, metal materials, such as aluminium and stainless steel, or may be selected as a combination of two or more of these materials. Among these materials, polyester, polypropylene, polyethylene and stainless steel are particularly preferable.

The opening of a mesh used in the venous blood filtering member 9 is preferably about 15 to 300 $\mu$m and, particularly preferably, about 20 to 200 $\mu$m. If the opening is larger than 300 $\mu$m, fine bubbles may pass through the mesh along with blood. If the opening is smaller than 15 $\mu$m, the resistance to passage of blood becomes so high that the level of blood in the filtering and foaming device 7b tends to be excessively high.

The venous blood filtering member 9 may be processed by a hydrophilization treatment such as a plasma treatment or coating with a hydrophilic polymeric material to further improve its blood permeability. In such a case, a hydrophilization treatment such as a plasma treatment may be performed on the basis of an ordinary method.

It is possible to effectively remove bubbles of, for example, about 20 $\mu$m or larger in diameter by using the venous blood filtering member 9 formed as described above.

Because the above-described venous blood filtering member 9 itself is low in rigidity, it is supported and fixed on a ladder-like frame member 12 in the arrangement shown in FIG. 4. The material of the frame member 12 may be the same as that of the venous blood lead-in tube 8 described above.

Preferably, the defoaming member 10 on which the same antifoaming agent as that described above is retained is placed above the venous blood filtering member 9. The material of the defoaming material 10 is also the same as that described above. The same antifoaming agent as that described above may also be retained on the venous blood filtering member 9 (on an upper portion thereof in particular) by the same retention method.

Preferably, the position 101 of the lower end surface of the defoaming member 10 is set close to or higher than the blood level (maximum blood level Lmax) reached by the maximum amount of blood storable in the blood reservoir 1.

According to the present invention, the blood reservoir 1 may be arranged without the above-described filtering and defoaming device 7b.

<Second Embodiment>

Figure 6:
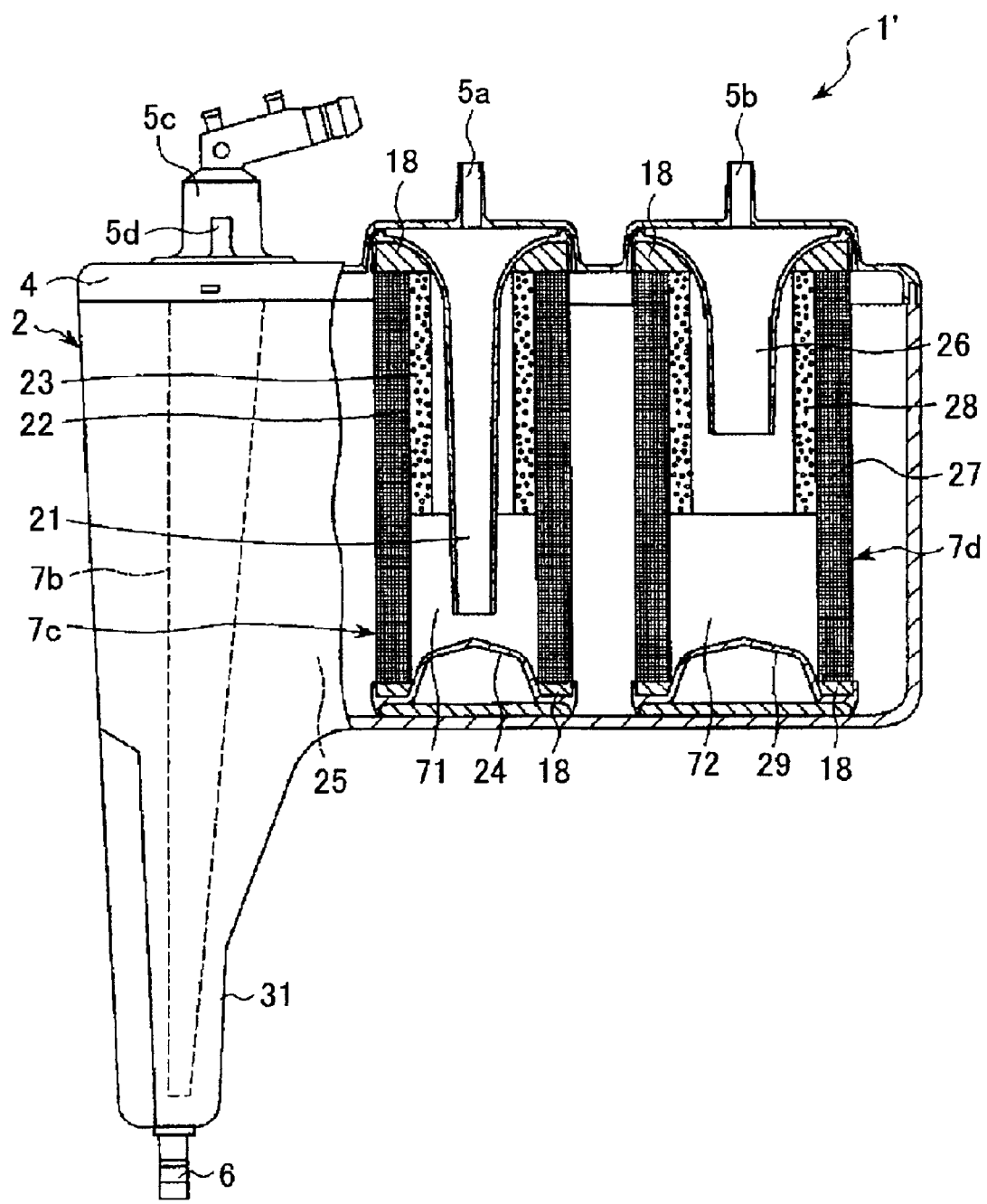
FIG. 6 is a side view partly in section of a blood reservoir which represents a second embodiment of the present invention.

FIG. 6 is a side view partly in section of a blood reservoir which represents a second embodiment of the present invention.

The blood reservoir of the second embodiment will be described with reference to FIG. 6 mainly with respect to points of difference from the above-described embodiment without repeating the description of the same details.

In FIG. 6, reference numeral 1' indicates a blood reservoir; 2, a housing; 4, a lid; 5a, a vented blood inlet; 5b, a suctioned blood inlet; 5c, a venous blood inlet; 5d, a priming solution inlet; 6, a blood outlet; 7b, 7c and 7d, filtering and defoaming devices; 18, a potting material; 21, a vented blood lead-in tube; 22, a vented blood filtering member; 23, a defoaming member; 24, a blood distributing member; 25, a blood reservoir space; 26, a suctioned blood lead-in tube; 27, a suctioned blood filtering member; 28, a defoaming member; 29, a blood distributing member; 31, a projecting portion; 71, a vented blood filtering chamber; and 72, a suctioned blood filtering chamber.

In FIG. 6, the blood reservoir 1' is the same as the above-described first embodiment except that a filtering and defoaming device 7c for filtering vented blood and removing bubbles from vented blood and a filtering and defoaming device 7d for filtering suctioned blood and removing bubbles from suctioned blood are provided in place of the filtering and defoaming device 7a of the blood reservoir 1. That is, the difference of this embodiment from the first embodiment resides in that a filtering and defoaming device for filtering and defoaming on vented blood and another filtering and defoaming device for filtering and defoaming on suctioned blood are provided as separate units.

The filtering and defoaming device 7c for filtering and defoaming on vented blood has a vented blood lead-in tube 21 having its upper end connected to the vented blood inlet 5a, a vented blood filtering member 22 placed around the vented blood lead-in tube 21, a defoaming member 23 placed along the inner surface of an upper portion of the vented blood filtering member 22, and a blood distributing member 24 placed at the lower end of the vented blood filtering member 22. A vented blood filtering chamber 71 is formed in the filtering and defoaming device 7c by being encircled by the vented blood filtering member 22.

The filtering and defoaming device 7d for filtering and defoaming on suctioned blood has a suctioned blood lead-in tube 26 having its upper end connected to the suctioned blood inlet 5b, a suctioned blood filtering member 27 placed around the suctioned blood lead-in tube 26, a defoaming member 28 placed along the inner surface of an upper portion of the suctioned blood filtering member 27, and a blood distributing member 29 placed at the lower end of the suctioned blood filtering member 27. A suctioned blood filtering chamber 72 is formed in the filtering and defoaming device 7d by being encircled by the suctioned blood filtering member 27.

In these filtering and defoaming devices 7c and 7d, the details of the filtering members 22 and 27, defoaming members 23 and 28, and the blood distributing members 24 and 29 are the same as those described above with respect to the filtering and defoaming device 7a of the first embodiment.

Preferably, the lower end of the vented blood lead-in tube 21 for leading vented blood into the filtering and defoaming device is extended downward relative to the lower end of the suctioned blood lead-in tube 26, thereby achieving a foaming reduction effect similar to that in the first embodiment.

In this embodiment, vented blood caused to flow into the filtering and foaming device 7c passes through the vented blood filtering member 22 without contacting foreign substances such as fat droplets, tissue fragments, denatured proteins and aggregates other than the ordinary blood contents, filtered off from suctioned blood by the suctioned blood filtering member 27 in the filtering and defoaming device 7d. Therefore the vented blood is not activated by interaction with these foreign substances. Consequently, total damage to blood to be fed (returned) after temporary storage in the blood reservoir 1' is reduced, thereby reducing harmful effects on the living body, as in the first embodiment.

Conditions in the vented blood filtering member 22 forming the vented blood filtering chamber 71 and conditions in the suctioned blood filtering member 27 forming the suctioned blood filtering chamber 72 are made different from each other to improve the above-described effect. The conditions in each filtering member are the effective area, material, shape, structure, size, and mesh opening of the filtering member, etc.

For example, since the rate of inflow of suctioned blood is ordinarily higher than that of vented blood flows, the effective area of the suctioned blood filtering member 27 for filtering suctioned blood is increased relative to that of vented blood filtering member 22 for filtering vented blood to improve the efficiency with which foreign substances and bubbles contained in suctioned blood are removed.

Also, the materials and the openings for the vented blood filtering member 22 and the suctioned blood filtering member 27 may be made different from each other by considering the difference in the amount of mixed foreign substances described above.

The total amount (total weight) of an antifoaming agent retained on the defoaming member 23 for defoaming on vented blood may be reduced relative to the total amount of an antifoaming agent retained on the defoaming member 28 for defoaming on suctioned blood to reduce the amount of the antifoaming agents mixed into blood during defoaming, thereby reducing damage to blood. That is, the amount of bubbles contained in vented blood is ordinarily smaller than that in suctioned blood and, therefore, the amount of the antifoaming agent for defoaming on vented blood can be reduced. If a difference is set between the amounts of the antifoaming agents retained on the two defoaming members 23 and 28 as described above, the total amount of the antifoaming agents mixed in blood can be reduced and an improved defoaming effect can be obtained with stability.

To set a difference between the total amounts of the antifoaming agents retained on the two defoaming members 23 and 28, the amounts of the retained antifoaming agents (the weights per unit volume) or the volumes of the defoaming members may be made different from each other or both the amounts of the retained antifoaming agents and the volumes of the defoaming members may be made different from each other.

The antifoaming agent for the defoaming member 23 and the antifoaming agent for the defoaming member 28 may have the same composition or different compositions (differing in the kinds and amounts of additives).

In this embodiment, as described above, the filtering and defoaming device for filtering and defoaming on vented blood and the filtering and defoaming device for filtering and defoaming on suctioned blood are provided as separate units, so that the various conditions in each filtering and defoaming device can be easily optimized with respect to the kind of blood, thus improving the condition of blood flowing out of the blood reservoir 1'.

In the above-described first embodiment, two different settings of conditions in the filtering member 15 and the amount of the retained antifoaming agent, corresponding to those in the second embodiment, may be made between the vented blood filtering chamber 71 and the suctioned blood filtering chamber 72 to achieve the same effect as that of the second embodiment.

<Third Embodiment>

Figure 7:
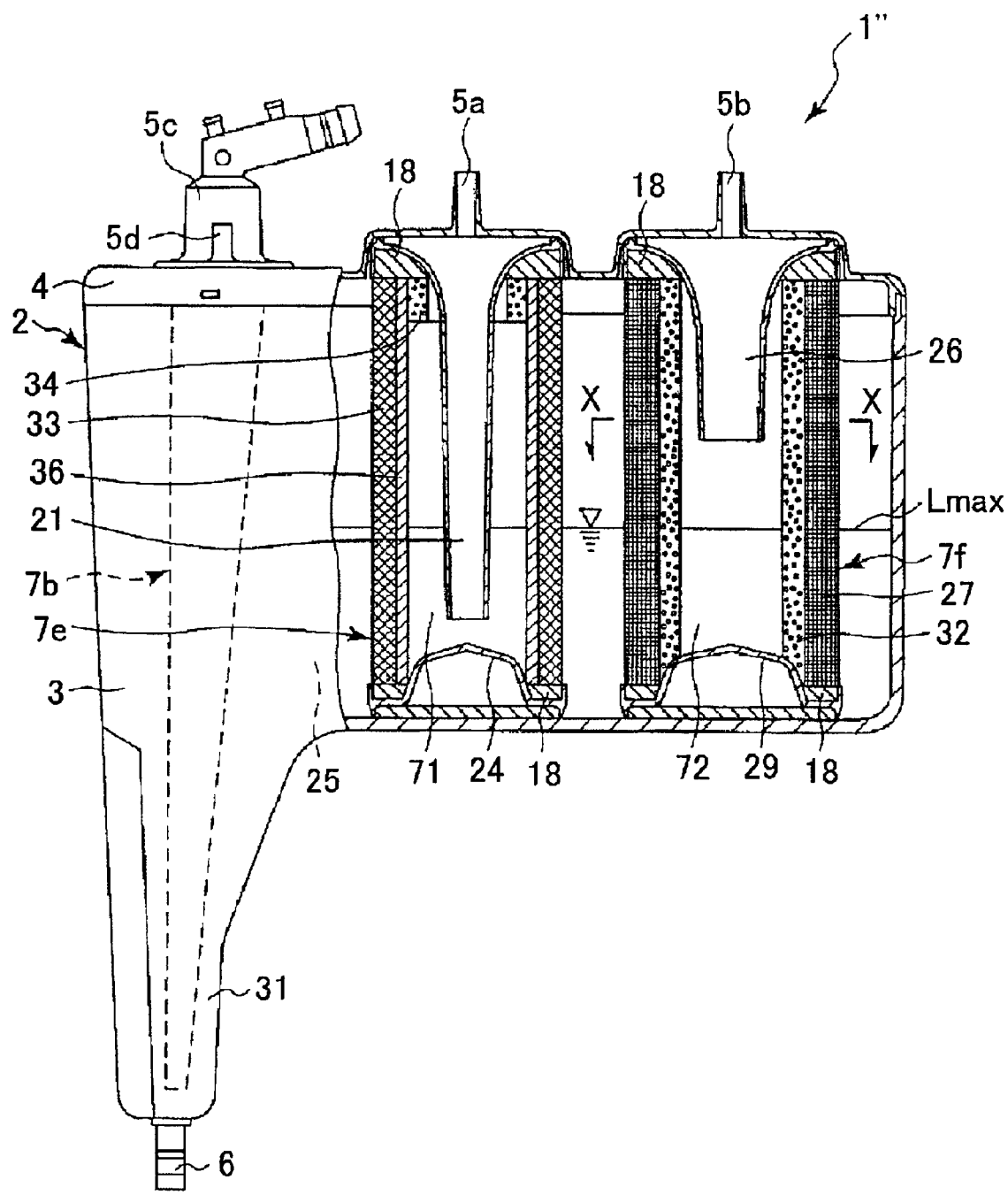
FIG. 7 is a side view partly in section of a blood reservoir which represents a third embodiment of the present invention.
Figure 8:
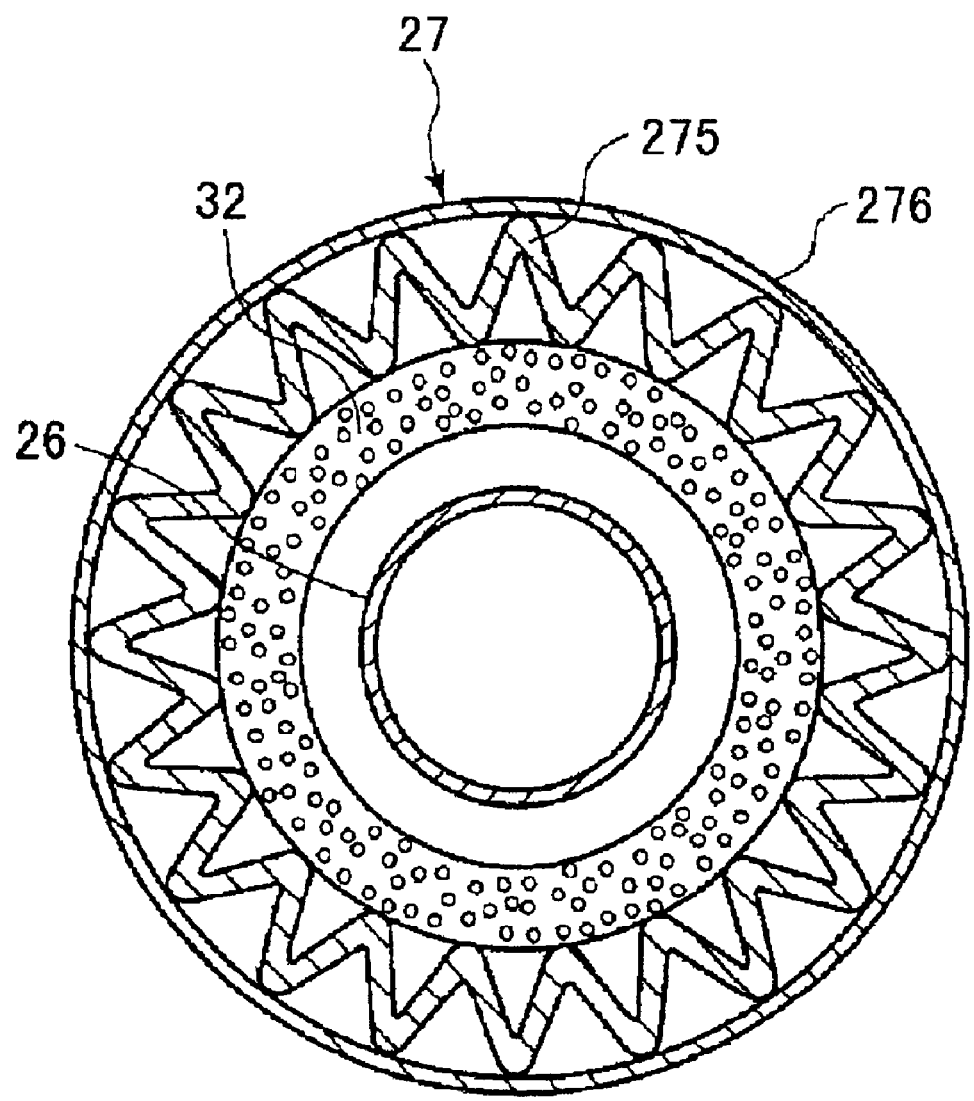
FIG. 8 is a cross-sectional view taken along the line X—X of FIG. 7.

FIG. 7 is a side view partly in section of a blood reservoir which represents a third embodiment of the present invention, FIG. 8 is a cross-sectional view taken along the line X—X of FIG. 7.

The blood reservoir of the third embodiment will be described with reference to FIG. 6 mainly with respect to points of difference from the above-described embodiment without repeating the description of the same details.

In FIG. 7, reference numeral 1" indicates a blood reservoir; 2, a housing; 3, a housing body; 4, a lid; 5a, a vented blood inlet; 5b, a suctioned blood inlet; 5c, a venous blood inlet; 5d, a priming solution inlet; 6, a blood outlet; 7b, 7e and 7f, filtering and defoaming devices; 18, a potting material; 21, a vented blood lead-in tube; 24, a blood distributing member; 25, a blood reservoir space; 26, a suctioned blood lead-in tube; 27, a suctioned blood filtering member; 29, a blood distributing member; 31, a projecting portion, 32 and 34, defoaming members; 33, a vented blood filtering member; 36, a frame member; 71, a vented blood filtering chamber; and 72, a suctioned blood filtering chamber.

In FIG. 7, the blood reservoir 1' is the same as the above-described first embodiment except that a filtering and defoaming device 7e for filtering vented blood and removing bubbles from vented blood and a filtering and defoaming device 7f for filtering suctioned blood and removing bubbles from suctioned blood are provided in place of the filtering and defoaming device 7a of the blood reservoir 1.

In the third embodiment, a filtering and defoaming device 7e for performing the filtering and defoaming on vented blood and a filtering and defoaming device 7f for performing the filtering and defoaming on suctioned blood are provided as separate units, as are those in the second embodiment. In the third embodiment, conditions in each of the two filtering and defoaming devices other than those described with respect to the second embodiment (the performance of the device) are modified according to the kind of blood.

The filtering and defoaming device 7f performs filtering and defoaming on suctioned blood flowing thereinto through the suctioned blood inlet 5b. The filtering and defoaming device 7f has a suctioned blood lead-in tube 26 having its upper end connected to the suctioned blood inlet 5b, a suctioned blood filtering member 27, a defoaming member 32 placed along the inner surface of the suctioned blood filtering member 27, and a blood distributing member 29.

In the filtering and defoaming devices 7f, the detail of the filtering member 27, the defoaming member 32, and the blood distributing member 29 are the same as those described above with respect to the filtering and defoaming device 7d of the second embodiment.

The details of the suctioned blood filtering member 27 are substantially the same as those of the filtering member 15 of the first embodiment described above. However, the suctioned blood filtering member 27 is, preferably, a depth filter (deep-bed filtration type) in which the filter member captures foreign substances at its inner portion. More preferably, it is a depth filter including nonwoven fabric. This is because the depth filter can capture a comparatively large amount of foreign substances and is therefore capable of effectively removing foreign substances from suctioned blood in which the contents of foreign substances are large.

FIG. 8 is a cross-sectional view of the suctioned blood filtering member 27. In FIG. 8 are illustrated the suctioned blood lead-in tube 26, the suctioned blood filtering member 27, the defoaming member 32, an inner layer 275, and an outer layer 276. The structure of the suctioned blood filtering member 27 is the same as that shown in FIG. 3.

In this embodiment, the defoaming member 32 is provided so as to cover the most of the inner surface of the suctioned blood filtering member 27 and is extended to a position below the blood level (maximum blood level Lmax) reached by the maximum amount of blood storable in the blood reservoir 1". That is, in the filtering and defoaming device 7f, an antifoaming agent also is provided below the maximum blood level Lmax to effectively remove bubbles in the blood as well as those above the liquid surface of blood.

A method of retaining an antifoaming agent for the defoaming member 32 placed in the filtering and defoaming device 7f is not exclusively used as a method of placing an antifoaming agent in the filtering and defoaming device 7f and any method may be used. For example, an antifoaming agent may be retained on the suctioned blood filtering member 27, and an antifoaming agent may be retained on both the defoaming member 32 and the suctioned blood filtering member 27.

The filtering and defoaming device 7e will be described mainly with respect to points of difference from the above-described filtering and defoaming devices 7c and 7e without repeating the description of the same details.

The filtering and defoaming device 7e performs filtering and defoaming on vented blood flowing thereinto through the vented blood inlet 5a. The filtering and defoaming device 7e has a vented blood lead-in tube 21 having its upper end communicating with the vented blood inlet 5a, a vented blood filtering member 33 placed in the periphery of the vented blood lead-in tube 21, a defoaming member 34 placed along the inner surface of an upper portion of the vented blood filtering member 33, and a blood distributing member 24 placed at the lower end of the vented blood filtering member 33. Blood vented from the vented blood inlet 5a flows into the vented blood filtering chamber 71 of the filtering and defoaming device 7e through the vented blood lead-in tube 21.

In this embodiment, as described above, the suctioned blood filtering member 27 and the vented blood filtering member 33 are provided as separate units to ensure that vented blood passes through the vented blood filtering member 33 without contacting foreign substances such as fat droplets, tissue fragments, denatured proteins and aggregates other than the ordinary blood contents, filtered off from suctioned blood. Therefore the vented blood is not activated by interaction with such foreign substances and is maintained in a less damaged state. Consequently, total damage to blood stored in the blood reservoir 1" is reduced, thereby reducing harmful effects on the living body.

Preferably, the suctioned blood filtering member 27 and the vented blood filtering member 33 are arranged by setting different conditions, as are those in the second embodiment. Conditions in each filter member can be optimized thereby with respect to suctioned blood or vented blood to further improve the condition of blood stored in the blood reservoir 1".

Preferably, the same kind of filtering member as the above-described venous blood filtering member 9 is used as the vented blood filtering member 33. As mentioned above, vented blood contains smaller amounts of foreign substances and bubbles, is less damaged and is generally the same as blood drawn off from the large veins. Therefore, the same kind of filtering member as the venous blood filtering member 9 is used to perform desired filtering and defoaming with efficiency and precise separation.

Preferably, the vented blood filtering member 33 is a screen filter (surface filtration type) in which the filter member captures foreign substances at its surface. The screen filter has a lower passage resistance and high blood permeability and is therefore capable of preventing activation of vented blood. The screen filter also has high opening accuracy and can effectively remove bubbles, etc.

The material and other particulars of the screen filter are the same as those of the above-described venous blood filtering member 9.

The defoaming member 34 in the filtering and defoaming device 7e is placed above the maximum blood level Lmax. In this embodiment, the defoaming member 34 is placed in the vicinity of the upper end of inner periphery of the vented blood filtering member 33.

This arrangement ensures that vented blood flowing into the filtering and defoaming device 7e through the vented blood inlet 5a does not contact the antifoaming agent retained on the defoaming member 34 in an ordinary situation. That is, vented blood flowing into the filtering and defoaming device 7e through the vented blood inlet 5a passes through the vented blood filtering member 33 without contacting the antifoaming agent. As mentioned above, vented blood contains a comparatively small amount of bubbles (in comparison with suctioned blood). Therefore, bubbles in vented blood can be sufficiently effectively removed by the vented blood filtering member 33 even though the blood is not brought into contact with the antifoaming agent.

Thus, in this embodiment, vented blood flowing into the filtering and defoaming device through the vented blood inlet 5a does not contact the antifoaming agent, so that the total amount of the antifoaming agent mixed into blood can be reduced. Thus, the effect of reducing damage to blood is further improved.

In the unlikely event that the amount of bubbles in the filtering and defoaming device 7e becomes excessively large, the bubbles are removed by contact with the defoaming member 34. That is, the defoaming member 34 is provided for emergency use. According to the present invention, the blood reservoir may be arranged without defoaming member 34.

In this embodiment, as described above, the antifoaming agent is also provided in the section of the filtering and defoaming device 7f below the maximum blood level Lmax. Therefore, not only bubbles above the liquid surface of blood but also bubbles in the blood can be effectively removed. (The condition of blood flowing out from the blood reservoir 1" is further improved thereby.)

Also, conditions in each filtering member are optimized with respect to suctioned blood or vented blood, thereby further improving the condition of blood stored in the blood reservoir 1".

Further, the same kind of filter member as the venous blood filtering member 9 is used as the vented blood filtering member 33, thereby enabling desired efficient and precise filtering separation and defoaming.

The blood reservoirs in accordance with embodiments of the present invention with reference to the accompanying drawings have been described. However, the present invention is not limited to the described embodiments. Each component of the blood reservoir can be replaced with a component of any different construction capable of performing the same function.

<Experimental Embodiments>

The blood reservoir of the present invention will be described further in detail according to specific embodiments of the present invention.

(Embodiment 1)

A blood reservoir of the construction shown in FIG. 6 was made. Various conditions for this blood reservoir are as shown in Table 1 below.

TABLE 1

| | |
|---|---|
| Maximum storable blood amount | 4000 ml |
| Materials for filtering members 22 and 27 | PET nonwoven fabric |
| Effective area of filtering member 22 | 300 cm$^2$ |
| Effective area of filtering member 27 | 500 cm$^2$ |
| Materials for defoaming members 23 and 28 | Polyurethane Foam (pore size: about 1 mm) |
| Kind of antifoaming agent | Silicone |
| Conditions of retention of antifoaming agent for defoaming member | Immersion for 10 seconds in 1% silicone/1000 ml Freon, followed by air-drying |
| Volume of defoaming member 23 | 30 cm$^3$ |
| Volume of defoaming member 28 | 50 cm$^3$ |

(Embodiment 2)

A blood reservoir of the construction shown in FIG. 7 was made. Various conditions in this blood reservoir are as shown in Table 2.

TABLE 2

| | |
|---|---|
| Maximum storable blood amount | 4000 ml |
| Material for suctioned blood filtering member 27 | PET nonwoven fabric |
| Effective area of suctioned blood filtering member 27 | 300 cm$^2$ |
| Material for vented blood filtering member 33 | PET mesh |
| Effective area of vented blood filtering member 33 | 300 cm$^2$ |
| Materials for defoaming members 32 and 34 | Polyurethane Foam (pore size: about 1 mm) |
| Kind of antifoaming agent | Silicone |
| Conditions of retention of antifoaming agent for defoaming member | Immersion for 10 seconds in 6% silicone/100 ml Freon, followed by air-drying |
| Volume of defoaming member 32 | 450 cm$^3$ |
| Volume of defoaming member 34 | 200 cm$^3$ |

(Comparative Example 1)

A blood reservoir was made whose construction differs from that of the blood reservoir shown in FIGS. 1 through 4 in that partition 19 and blood lead-in tube 20 are not provided. That is, in the blood reservoir in this comparative example, the blood in flowing from the vented blood inlet 5a and the blood flowing from the suctioned blood inlet 5b join into one before passage through the filtering member 15. Conditions for this blood reservoir are as shown in Table 3 below. The same reference numerals as those for the components of the blood reservoir shown in FIGS. 1 through 4 are also used for the components of the blood reservoir in Comparative Example 1 for convenience sake.

TABLE 3

| | |
|---|---|
| Maximum storable blood amount | 4000 ml |
| Material for filtering member 15 | PET nonwoven fabric |
| Effective area of filtering member 15 | 800 cm$^2$ |
| Material for defoaming member 16 | Polyurethane Foam (pore size: about 1 mm) |
| Kind of antifoaming agent | Silicone |
| Conditions of retention of antifoaming agent for defoaming member | Immersion for 10 seconds in 1% silicone/1000 ml Freon, followed by air-drying |
| Volume of defoaming member 16 | 80 cm$^3$ |

(Comparative Example 2)

A blood reservoir was made whose construction differs from that of the blood reservoir in the second example in that the suctioned blood and the vented blood flow into the common filtering and defoaming device to be filtered and defoamed. That is, in the blood reservoir in this comparative example, the cardiotomy reservoir section has a single filtering and defoaming device, and both blood suctioned from the suctioned blood inlet and blood vented from the vented blood inlet flow into this filtering and defoaming device. The structure of this filtering and defoaming device is generally the same as that of the filtering and defoaming device 7b in the blood reservoir of the second embodiment. Various conditions for the blood reservoir, etc., in the blood reservoir in Comparative Example 2 are as shown in Table 4 below.

TABLE 4

| | |
|---|---|
| Maximum storable blood amount | 4000 ml |
| Material for filtering member | PET nonwoven fabric |
| Effective area of filtering member | 800 cm² |
| Material for defoaming member | Polyurethane Foam (pore size: about 1 mm) |
| Kind of antifoaming agent | Silicone |
| Conditions of retention of antifoaming agent for defoaming member | Immersion for 10 seconds in 6% silicone/100 ml Freon, followed by air-drying |
| Volume of defoaming member | 200 cm³ |

Figure 9:
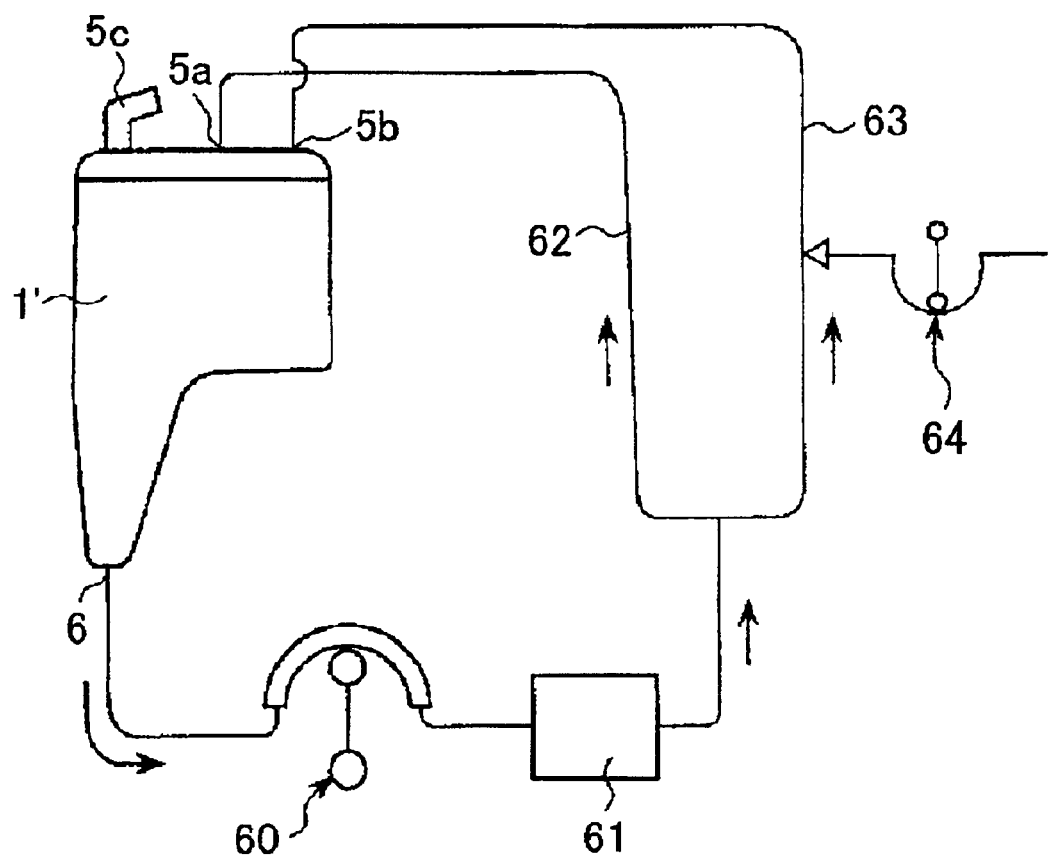
FIG. 9 is a diagram showing a blood circulation circuit used in an experiment made on examples of the present invention.

An experiment described below was made on each of the blood reservoirs in the above-mentioned embodiments of the present invention and the comparative examples. FIG. 9 is a circuit diagram showing blood circulation in the experiment.

The circuit shown in FIG. 9 is formed by the blood reservoir 1', the vented blood inlet 5a, the suctioned blood inlet 5b, the venous blood inlet 5c, the blood outlet 6, a roller pump 60, a heat exchanger 61, a vent line 62, a suction line 63, and an air mixing line 64.

Each of the blood reservoirs in the embodiments of the present invention and the comparative examples was connected to the circulation circuit shown in FIG. 9. That is, in this circulation circuit, the roller pump 60 and the heat exchanger 61 are provided in a line connected to the blood outlet 6. This line was formed so as to diverge into two lines, i.e., the vent line 62 and the suction line 63 downstream of the heat exchanger 61. The tube of the vent line 62 was connected to the vented blood inlet 5a, and the tube of the suction line 63 was connected to the suctioned blood inlet 5b. The air mixing line 64 was provided at an intermediate point in the suction line 63.

This circulation circuit was filled with a mixed solution prepared by mixing 200 ml of heparinized human fresh blood and 350 ml of lactated Ringer's solution, and the solution was perfused (circulated) in the circuit at an average flow rate of 1000 ml/min while the blood temperature was maintained at 37° C. During this perfusion, air (bubbles) was mixed in the blood flowing through the suction line 63 at a rate of 10 ml/min in the first embodiment and the first comparative example and at a rate of 100 ml/min in the second embodiment and the second comparative example. After a whole, generation of aggregates filtered off from the blood in the suction line 63 was observed in the filtering and defoaming device 7d in the first embodiment, in the filtering and defoaming device 7f in the second embodiment, and in the filtering and defoaming devices in the comparative examples.

After a lapse of 2 hours from the start of perfusion, the blood at a point closest to the blood outlet 6 in each circulation circuit was sampled, and the number of platelets, the number of leukocytes, the amount of β-TG and the amount of granulocyte elastase in each sampled blood were measured. β-TG is an agent produced by activation of platelets, and granulocyte elastase is an agent produced by activation of leukocytes.

Table 5 shows the results of measurements of the first embodiment and the first comparative example, and Table 6 shows the results of measurements of the second embodiment and the second comparative example. Each of the number of platelets and the number of leukocytes is shown as a proportion to the measured value obtained before perfusion (% of pre).

TABLE 5

| | Number of platelets | Number of leukocytes | β-TG [mg/dl] | Granulocyte elastase [μg/l] |
|---|---|---|---|---|
| Embodiment 1 | 87% | 49% | 294 | 510 |
| Comparative Example 1 | 63% | 31% | 588 | 1050 |

TABLE 6

| | Number of platelets | Number of leukocytes | β-TG [mg/dl] | Granulocyte elastase [μg/l] |
|---|---|---|---|---|
| Embodiment 2 | 87% | 78% | 196 | 58 |
| Comparative Example 2 | 52% | 38% | 1047 | 2140 |

As can be understood from the results shown in Tables 5 and 6, after the blood circulation the number of platelets and the number of leukocytes remained in the circulation circuits using the blood reservoirs in the embodiments of the present invention were much larger than those in the circulation circuits using the blood reservoirs in the comparative examples. Also, the amount of β-TG and the amount of granulocyte elastase in the circulation circuits using the blood reservoirs in the embodiments of the present invention were much smaller than those in the circulation circuits using the blood reservoirs in the comparative examples. This means that the degree of activation of blood in the circulation circuits using the blood reservoirs in the embodiments of the present invention was lower. As is apparent from these experiment results, the amounts of damage to blood in the circulation circuits using the blood reservoirs in the embodiments of the present invention were advantageously smaller than those in the circulation circuits using the blood reservoirs in the comparative examples.

According to the present invention, as described above, activation of vented blood flowing into the blood reservoir can be limited, so that the blood reservoir has the effect of reducing damage to blood stored therein.

Also, mixing of an antifoaming agent into vented blood flowing into the blood reservoir can be prevented to reduce damage to stored blood.

In a case where conditions for the suctioned blood filtering member and conditions for the vented blood filtering member are made different from each other, for example, a screen filter is used as the suctioned blood filtering member while a depth filter is used as the vented blood filtering member, each of vented blood and suctioned blood can be filtered under conditions optimized according to the characteristics of the respective bloods, thereby further improving the above-described effects.

Further, in the case where defoaming means is provided, if the total amount of a retained antifoaming agent for defoaming in the vented blood filtering chamber and the total amount of a retained antifoaming agent for defoaming in the suctioned blood filtering chamber are made different from each other, damage to stored blood can be further reduced.

What is claimed is:

1. A blood reservoir comprising:
a housing having a vented blood inlet through which blood vented from the interior of a heart flows in, a suctioned blood inlet through which blood suctioned from the outside of the heart flows in, and a blood outlet;

a vented blood filtering unit provided in said housing, the vented blood filtering unit having a vented blood filtering member configured to filter the vented blood flowing in through said vented blood inlet;

a suctioned blood filtering unit provided in said housing, the suctioned blood filtering unit having a suctioned blood filtering member configured to filter the suctioned blood flowing in through said suctioned blood inlet; and an antifoaming agent placed in said suctioned blood filtering unit, said antifoaming agent placed at a position which contacts the suctioned blood flowing in through said suctioned blood inlet, wherein the vented blood flowing in through said vented blood inlet passes through said vented blood filtering member without contacting said antifoaming agent and foreign substances filtered off from the suctioned blood.

2. A blood reservoir according to claim 1, wherein at least one condition set in said vented blood filtering member and at least one condition set in said suctioned blood filtering member are different from each other.

3. A blood reservoir according to claim 1, wherein said vented blood filtering member comprises a screen filter.

4. A blood reservoir according to claim 1, wherein said suctioned blood filtering member comprises a depth filter.

5. A blood reservoir according to claim 1, wherein said suctioned blood filtering member comprises nonwoven fabric.

6. A blood reservoir according to claim 1, wherein the effective area of said vented blood filtering member and the effective area of said suctioned blood filtering member are different from each other.

7. A blood reservoir according to claim 1, wherein said antifoaming agent is retained on at least one of a retaining member provided in said suctioned blood filtering unit and said suctioned blood filtering member.

8. A blood reservoir according to claim 1, wherein said antifoaming agent is also provided below a maximum blood level.

9. A blood reservoir according to claim 1, wherein said vented blood filtering unit has an antifoaming agent placed at a position above the maximum blood level such that the vented blood flowing in through said vented blood inlet does not contact the antifoaming agent in an ordinary situation.

10. A blood reservoir according to claim 1, further comprising a vented blood lead-in tube for leading blood from said vented blood inlet into said vented blood filtering chamber, and a suctioned blood lead-in tube for leading blood from said suctioned blood inlet into said suctioned blood filtering chamber.

11. A blood reservoir according to claim 10, wherein said vented blood lead-in tube is extended downward relative to said suctioned blood lead-in tube.

12. A blood reservoir according to claim 1, wherein said housing further has a venous blood inlet through which blood from a large vein flows in, and a venous blood filtering unit having a venous blood filtering member for filtering blood flowing through the venous blood inlet is provided in said housing.

13. A blood reservoir according to claim 12, wherein the same kind of filtering member as said venous blood filtering member is used as said vented blood filtering member.

14. A blood reservoir comprising:

a housing having a vented blood inlet through which blood vented from the interior of a heart flows in, a suctioned blood inlet through which blood suctioned from outside the heart flows in, and a blood outlet;

a filtering unit provided in said housing, the filtering unit having a filtering member configured to filter the blood flowing in;

a vented blood filtering chamber communicating with said vented blood inlet and formed at least partially by said filtering member forming a vented blood filtering member; and a suctioned blood filtering chamber communicating with said suctioned blood inlet and formed at least partially by said filtering member forming a suctioned blood filtering member, wherein the vented blood flowing into said housing passes through said filtering member without contacting foreign substances filtered off from the suctioned blood.

15. A blood reservoir according to claim 14, wherein said vented blood filtering chamber and said suctioned blood filtering chamber are formed by using a partition to separate a space encircled by the same filtering member into two.

16. A blood reservoir according to claim 14, wherein said vented blood filtering chamber and said suctioned blood filtering chamber are formed by separate filtering members.

17. A blood reservoir according to claim 16, wherein at least one condition set in the vented blood filtering member provided as the filtering member forming said vented blood filtering chamber and at least one condition set in the suctioned blood filtering member provided as the filtering member forming said suctioned blood filtering chamber are different from each other.

18. A blood reservoir according to claim 14, wherein said suctioned blood filtering member comprises nonwoven fabric.

19. A blood reservoir according to claim 14, wherein the effective area of said vented blood filtering member and the effective area of said suctioned blood filtering member are different from each other.

20. A blood reservoir according to claim 14, further comprising defoaming means in which an antifoaming agent is retained on at least one of said filtering member and a retaining member.

21. A blood reservoir according to claim 20, wherein said defoaming means comprises an antifoaming agent retained on at least one of the filtering member forming said vented blood filtering chamber and a retaining member placed on said vented blood filtering chamber, and an antifoaming agent retained on at least one of the filtering member forming said suctioned blood filtering chamber and a retaining member placed on said suctioned blood filtering chamber.

22. A blood reservoir according to claim 21, wherein the total amount of said antifoaming agent retained on at least one of the filtering member forming said vented blood filtering chamber and a retaining member placed on said vented blood filtering chamber, and the total amount of said antifoaming agent retained on at least one of the filtering member forming said suctioned blood filtering chamber and a retaining member placed on said suctioned blood filtering chamber are different from each other.

23. A blood reservoir according to claim 14, further comprising a vented blood lead-in tube for leading blood from said vented blood inlet into said vented blood filtering chamber, and a suctioned blood lead-in tube for leading blood from said suctioned blood inlet into said suctioned blood filtering chamber.

24. A blood reservoir according to claim 23, wherein said vented blood lead-in tube is arranged so as to extend downward relative to said suctioned blood lead-in tube.

25. A blood reservoir according to claim 14, wherein said housing has a venous blood inlet through which blood from a large vein flows in, and a venous blood filtering chamber communicating with said venous blood inlet and formed at least partially by said filtering member.

26. A method of introducing blood into a blood reservoir that comprises a housing having a vented blood inlet, a suctioned blood inlet, a blood outlet, and a filtering unit for filtering blood flowing into the housing, the method comprising:

introducing blood vented from the interior of a heart into a vented blood filtering chamber in the housing by way of said vented blood inlet, said vented blood filtering chamber being formed at least partially by said filtering unit;

introducing blood suctioned from outside the heart into a suctioned blood filtering chamber in the housing by way of said suctioned blood inlet, said suctioned blood filtering chamber being formed at least partially by said filtering unit;

the vented blood introduced into the vented blood filtering chamber by way of said vented blood inlet not including suctioned blood suctioned from outside the heart; and filtering the vented blood and the suctioned blood by virtue of the vented blood and the suctioned blood passing through said filtering unit.

* * * * *

UNITED STATES PATENT AND TRADEMARK OFFICE
CERTIFICATE OF CORRECTION

PATENT NO. : 6,908,446 B2
APPLICATION NO. : 09/997171
DATED : June 21, 2005
INVENTOR(S) : Kenji Yokoyama et al.

It is certified that error appears in the above-identified patent and that said Letters Patent is hereby corrected as shown below:

Title Page, Item (73) Assignee: change "Termo" to --Terumo--.

Signed and Sealed this

Twenty-sixth Day of June, 2007

JON W. DUDAS
*Director of the United States Patent and Trademark Office*